United States Patent
Williams et al.

(10) Patent No.: US 11,812,959 B2
(45) Date of Patent: Nov. 14, 2023

(54) DYNAMICALLY MATCHING INPUT AND OUTPUT SHAFT SPEEDS OF ARTICULATING ADAPTER ASSEMBLIES FOR SURGICAL INSTRUMENTS

(71) Applicant: Covidien LP, Mansfield, MA (US)

(72) Inventors: Justin Williams, Southbury, CT (US); Anthony Sgroi, Southbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/692,394

(22) Filed: Mar. 11, 2022

(65) Prior Publication Data
US 2022/0192664 A1    Jun. 23, 2022

Related U.S. Application Data

(62) Division of application No. 15/876,594, filed on Jan. 22, 2018, now Pat. No. 11,272,929.
(Continued)

(51) Int. Cl.
*A61B 34/30* (2016.01)
*A61B 17/072* (2006.01)
(Continued)

(52) U.S. Cl.
CPC ...... *A61B 17/072* (2013.01); *A61B 17/07207* (2013.01); *A61B 34/35* (2016.02);
(Continued)

(58) Field of Classification Search
CPC .. A61B 2017/0069; A61B 2017/00398; A61B 2017/00017; A61B 17/07207
See application file for complete search history.

(56) References Cited

U.S. PATENT DOCUMENTS 2,777,340 A    1/1957    Hettwer et al.
2,957,353 A    10/1960    Babacz
(Continued)

FOREIGN PATENT DOCUMENTS

CA    2451558 A1    1/2003
CN    1547454 A    11/2004
(Continued)

OTHER PUBLICATIONS

Extended European Search Report corresponding to International Application No. EP 14 18 4882.0 dated May 12, 2015.
(Continued)

*Primary Examiner* — Andrew M Tecco
(74) *Attorney, Agent, or Firm* — Carter, DeLuca & Farrell LLP

(57) ABSTRACT

A surgical system includes a power source, a handle housing, a motor, an adapter assembly, an end effector, and a correction unit. The motor is disposed within the handle housing and is in electrical communication with the power source. The adapter assembly is operably coupled to the handle housing and supports an input and an output shaft coupled by the universal joint. The input shaft is in mechanical communication with the motor. The end effector is coupled to the adapter assembly and is selectively articulatable relative to the adapter assembly. The correction unit is in electrical communication with the power source and the motor and is configured to adjust the input shaft speed of the input shaft to maintain a substantially constant output shaft speed of the output shaft as the end effector articulates relative to the adapter assembly.

20 Claims, 10 Drawing Sheets

Related U.S. Application Data

(60) Provisional application No. 62/466,415, filed on Mar. 3, 2017.

(51) Int. Cl.
  *A61B 34/35* (2016.01)
  *A61B 17/00* (2006.01)
  *A61B 17/29* (2006.01)
  *A61B 90/00* (2016.01)

(52) U.S. Cl.
  CPC . *A61B 17/2909* (2013.01); *A61B 2017/00017* (2013.01); *A61B 2017/0046* (2013.01); *A61B 2017/0069* (2013.01); *A61B 2017/00212* (2013.01); *A61B 2017/00367* (2013.01); *A61B 2017/00398* (2013.01); *A61B 2017/00473* (2013.01); *A61B 2017/00477* (2013.01); *A61B 2017/00482* (2013.01); *A61B 2017/2927* (2013.01); *A61B 2090/067* (2016.02); *A61B 2090/0811* (2016.02)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |

(56) References Cited

U.S. PATENT DOCUMENTS

| | | | |
|---|---|---|---|
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,827,134 B2 * | 9/2014 | Viola ............... A61B 17/07207 227/176.1 |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |

(56) References Cited

U.S. PATENT DOCUMENTS

| | | |
|---|---|---|
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 10,426,321 B2* | 10/2019 | Sholev ............... A61B 1/00149 |
| 11,272,929 B2 | 3/2022 | Williams et al. |
| 2001/0031975 A1 | 10/2001 | Whitman |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0029978 A1* | 2/2005 | Oleynikov ............ A61B 1/041 318/568.12 |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton, IV et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1* | 4/2009 | Zemlok ............ A61B 17/07207 227/175.2 |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0041263 A1* | 2/2012 | Sholev ................. A61B 90/98 600/118 |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2014/0374464 A1* | 12/2014 | Viola ................. A61B 17/068 227/177.1 |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |

(56) References Cited

U.S. PATENT DOCUMENTS

| | | | |
|---|---|---|---|
| 2015/0164502 A1 | 6/2015 | Richard et al. | |
| 2015/0201931 A1 | 7/2015 | Zergiebel et al. | |
| 2015/0209061 A1* | 7/2015 | Johnson | A61B 34/76 606/171 |
| 2015/0272577 A1 | 10/2015 | Zemlok et al. | |
| 2015/0297199 A1* | 10/2015 | Nicholas | A61B 17/00 606/1 |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0333676 A1* | 11/2015 | Liu | H02P 7/29 318/490 |
| 2015/0342601 A1 | 12/2015 | Williams et al. | |
| 2015/0342603 A1 | 12/2015 | Zergiebel et al. | |
| 2015/0351769 A1* | 12/2015 | Lee | A61B 17/1155 227/179.1 |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera | |
| 2016/0113648 A1 | 4/2016 | Zergiebel et al. | |
| 2016/0113649 A1 | 4/2016 | Zergiebel et al. | |
| 2016/0242631 A1* | 8/2016 | Sholev | A61B 1/00149 |
| 2016/0296216 A1* | 10/2016 | Nicholas | A61B 17/00 |
| 2017/0020614 A1* | 1/2017 | Jackson | A61B 34/30 |

FOREIGN PATENT DOCUMENTS

| | | | |
|---|---|---|---|
| CN | 1957854 | A | 5/2007 |
| CN | 101495046 | A | 7/2009 |
| CN | 102247182 | A | 11/2011 |
| DE | 102008053842 | A1 | 5/2010 |
| EP | 0705571 | A1 | 4/1996 |
| EP | 1563793 | A1 | 8/2005 |
| EP | 1769754 | A1 | 4/2007 |
| EP | 2263568 | A2 | 12/2010 |
| EP | 2316345 | A1 | 5/2011 |
| EP | 2668910 | A2 | 12/2013 |
| EP | 2937047 | A1 | 10/2015 |
| EP | 3078333 | A2 | 10/2016 |
| ES | 2333509 | A1 | 2/2010 |
| JP | 2005125075 | A | 5/2005 |
| KR | 20120022521 | A | 3/2012 |
| WO | 2009039506 | A1 | 3/2009 |
| WO | 2011108840 | A2 | 9/2011 |
| WO | 2012040984 | A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report dated Aug. 14, 2018 issued in corresponding EP Appln. No. 18159457.3.

* cited by examiner

DYNAMICALLY MATCHING INPUT AND OUTPUT SHAFT SPEEDS OF ARTICULATING ADAPTER ASSEMBLIES FOR SURGICAL INSTRUMENTS

CROSS-REFERENCE TO RELATED APPLICATIONS

This application is a divisional application of U.S. patent application Ser. No. 15/876,594, filed Jan. 22, 2018, which claims the benefit of U.S. Provisional Patent Application Ser. No. 62/466,415, filed Mar. 3, 2017, the entire disclosure of each of which is incorporated by reference herein.

TECHNICAL FIELD

The present disclosure generally relates to adapter assemblies for use in surgical systems. More specifically, the present disclosure relates to dynamically matching input and output shaft speeds of articulating adapter assemblies that electrically and mechanically interconnect electromechanical surgical devices and surgical end effectors.

BACKGROUND

In order to accommodate the need for clinicians to quickly and easily change the type of end effector being utilized during a surgical procedure, various adapter assemblies have been developed that interconnect electromechanical surgical devices with surgical end effectors. Typically, the adapter assemblies are releasably couplable to an electromechanical surgical device and are capable of converting rotational motion to linear motion or transmitting rotational inputs from the electromechanical surgical device to linear driving force in order to operate the surgical end effector attached to the electromechanical surgical device.

As can be appreciated, there is minimal space to maneuver the electromechanical surgical device within a patient's body cavity, and therefore, clinicians often have difficulty placing the end effector of the electromechanical surgical device in a position to effectively treat an area of interest. To enable more effective use of these electromechanical surgical devices, many of the existing adapter assemblies include an articulating joint that operably couples the end effector to the adapter assembly. These articulating joints must include a means for transmitting the rotational motion of the electromechanical surgical device across the articulating joint in order for the end effector to operate. Existing surgical devices have employed numerous types of couplings capable of transmitting rotational motion to the end effector while permitting the end effector to articulate with respect to the remainder of the adapter assembly. Many couplings known in the art introduce variations in the rotational velocity of the coupling output, often following a sinusoidal profile and the severity of which depends on the articulation angle of the end effector. The resulting non-uniform application of force transmits lumpy or jolting feedback through the clinician's hand. Current methods of alleviating this phenomenon require the use of additional couplings to cancel out variations in rotational velocity or the use of expensive, more complex, couplings that transmit rotational motion linearly, increasing the complexity and cost of the adapter assemblies.

SUMMARY

According to an aspect of the present disclosure, a surgical system is provided, the surgical system including, a power source, a handle housing, a motor disposed within the handle housing and in electrical communication with the power source, an adapter assembly operably coupled to the handle housing and supporting an input shaft and an output shaft coupled by a universal joint, the input shaft being in mechanical communication with the motor and rotatable in response to actuation of the motor, an end effector coupled to the adapter assembly and selectively articulatable relative to the adapter assembly, and a correction unit in electrical communication with the power source and the motor. The correction unit is configured to adjust the input shaft speed to maintain a substantially constant output shaft speed as the end effector articulates relative to the adapter assembly.

In aspects, the surgical system may further include an articulation sensor configured to measure an articulation angle of the universal joint as the end effector articulates relative to the adapter assembly. The articulation angle is defined between the input and output shafts of the universal joint.

In other aspects, the articulation sensor may include an accelerometer, a rotary encoder, an optical encoder, a magnetic encoder, a linear encoder, a Hall Effect sensor, a linear variable differential transformer, an inertial measurement unit, a microelectromechanical system, a gyroscope, or combinations thereof.

In some aspects, the surgical system may include a rotation sensor configured to measure rotational positioning of the universal joint. In certain aspects, the rotation sensor may include a counter, an encoder, a gyroscope, or combinations thereof.

In aspects, the surgical system may include a plurality of motor speed profiles stored within a memory associated with the correction unit. Each motor speed profile of the plurality of motor speed profiles may correspond to an articulation angle of the universal joint.

In some aspects, the end effector may include a staple cartridge assembly and an anvil assembly.

In other aspects, the surgical system may include a processor disposed within the handle assembly in electrical communication with the correction unit and configured to execute instructions stored on the memory to instruct the correction unit to adjust an output speed of the motor.

According to another aspect of the present disclosure, a method of operating a surgical system includes articulating an end effector relative to an adapter assembly via a universal joint rotatably disposed between the end effector and the adapter assembly, measuring an articulation angle of the universal joint, identifying a motor speed profile stored within a memory associated with a correction unit corresponding to the measured articulation angle of the universal joint, and manipulating an output speed of a motor operably coupled to the universal joint, according to the motor speed profile, to generate a substantially constant output speed from the universal joint.

In aspects, the method may include measuring a rotational position of the universal joint.

In other aspects, identifying a motor speed profile may include identifying a motor speed profile stored within a memory associated with the correction unit corresponding to the measured articulation angle and measured rotational position of the universal joint.

In certain aspects, the method may include firing a plurality of fasteners from the end effector. In aspects, firing a plurality of fasteners may include firing a plurality of surgical staples from a cartridge assembly disposed in the end effector.

In other aspects, measuring the articulation angle of the universal joint may include measuring the articulation angle of the universal joint using an articulation sensor operably coupled to the universal joint.

In aspects, measuring the rotational position of the universal joint may include measuring the rotational position of the universal joint using a rotation sensor operably coupled to the universal joint.

In some aspects, identifying a motor speed profile may include identifying a motor speed profile from a plurality of motor speed profiles stored within the memory associated with the correction unit.

In certain aspects, manipulating an output speed of the motor may include identifying a location within the identified motor speed profile based on the measured rotational position of the universal joint. In aspects, manipulating an output speed of the motor may include starting the motor at a speed associated with the identified location within the identified motor speed profile.

In other aspects, measuring the rotational position of the universal joint may include measuring the rotational position of the universal joint using a rotary encoder operably coupled to the universal joint.

In aspects, measuring the articulation angle of the universal joint may include measuring the articulation angle of the universal joint using an encoder.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
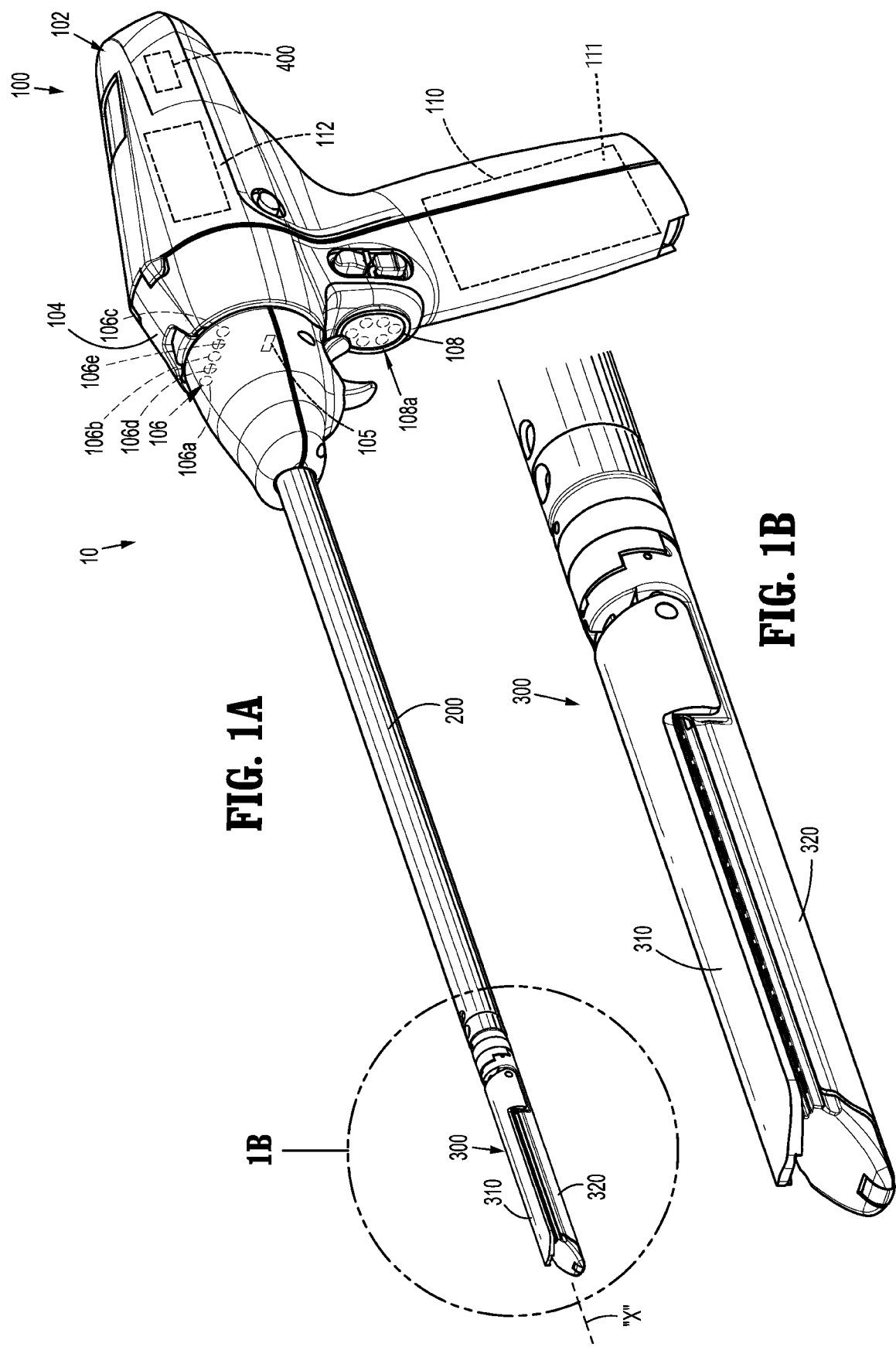
FIG. 1A is a perspective view of an electromechanical surgical system in accordance with the principles of the present disclosure, the electromechanical surgical system having an end effector shown in an unarticulated and clamped position.
FIG. 1B is an enlarged, perspective view of the indicated area of detail shown in FIG. 1A.

The electromechanical surgical systems of the present disclosure include surgical devices in the form of powered handheld electromechanical instruments configured for selective attachment to different adapter assemblies having an end effector. The end effectors are each configured for actuation and manipulation by the powered handheld electromechanical surgical instrument. In particular, the adapter assemblies are configured to convert rotational motion outputted by the powered handheld electromechanical surgical instrument into linear motion to fire surgical staples, clips, or the like. One or more couplings are utilized to enable articulation of the end effector relative to the adapter while simultaneously transmitting rotational motion. As can be appreciated, couplings, such as a universal joint, introduce variations in the rotational velocity of the output of the coupling relative to the input to the coupling. These variations increase in severity with a corresponding increase in articulation angle.

To combat this issue, a second coupling is typically introduced in series with the first coupling to effectively cancel out the variations in rotational velocity outputted by the coupling. However, additional couplings require additional space and introduce additional complexity to the system. The electromechanical surgical systems of the present disclosure utilize a single universal joint to transmit the rotational motion over the articulation joint. To account for variations in rotational velocity across the universal joint, a correction unit adjusts the output speed of a motor disposed within the powered handheld electromechanical instrument based on the articulation angle of the end effector and the rotational position of the universal joint. In this manner, the output speed of the motor is adjusted to increase or decrease in speed for eliminating the sinusoidal velocity profile at the output of the universal joint.

Embodiments of the presently disclosed electromechanical surgical systems, surgical devices/handle assemblies, adapter assemblies, and/or end effectors/loading units are described in detail with reference to the drawings, in which like reference numerals designate identical or corresponding elements in each of the several views. As used herein, the term "distal" refers to that portion of structure farther from the user, while the term "proximal" refers to that portion of the structure closer to the user. As used herein, the term "clinician" refers to a doctor, nurse, or other care provider and may include support personnel. In the following description, well-known functions or constructions are not described in detail to avoid obscuring the present disclosure in unnecessary detail.

Figure 2:
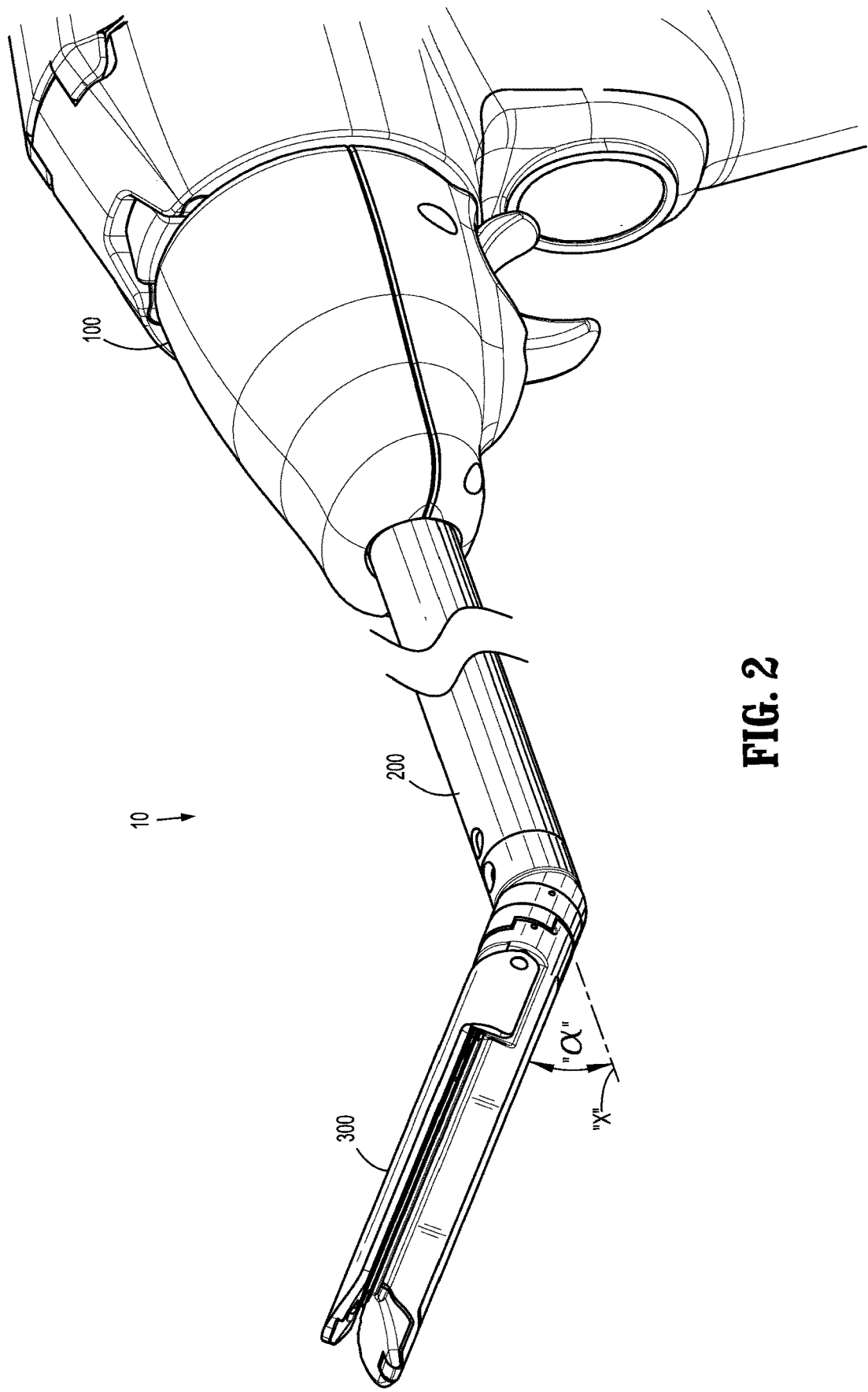
FIG. 2 is an enlarged, front, perspective view of a portion of the electromechanical surgical system of FIG. 1A, the end effector thereof shown in an articulated condition.

With reference to FIGS. 1A-2, an electromechanical surgical system is provided in accordance with the present disclosure and generally identified by reference numeral 10. The electromechanical surgical system 10 includes a surgical device 100, an adapter assembly 200, and a surgical loading unit (e.g., multiple or single-use loading unit) or end effector 300. The surgical device 100 is configured for selective connection with the adapter assembly 200 and, in turn, the adapter assembly 200 is configured for selective connection with the end effector 300. In embodiments, the surgical device 100 and the adapter assembly 200 may cooperate to actuate the end effector 300.

The surgical device 100 of the electromechanical surgical system 10 includes a handle housing 102 having a circuit board (not shown) and one or more motors 112 situated therein. The circuit board is configured to control the various operations of the surgical device 100. The handle housing 102 defines a cavity therein (not shown) configured to removably receive a power source such as a rechargeable battery 110 therein. The battery 110 is configured to supply power to any of the electrical components of the surgical device 100. In some embodiments, the surgical device 100 may couple to an external power source such as an AC outlet or generator. For an example of a generator, reference can be made to U.S. Pat. No. 8,784,410 to Dunning, the entire disclosure of which is incorporated by reference herein.

The handle housing 102 of the surgical device 100 provides a housing in which the one or more motors 112 are situated. Each motor 112 is configured to drive one or more shafts and/or gear components in order to perform the various operations of the surgical device 100. In particular, the one or more motors 112 of the surgical device 100 are configured: to drive the various shafts and/or gear components in order to selectively articulate the end effector 300 of the electromechanical surgical system 10 about a longitudinal axis "X" and relative to a distal end portion of the adapter assembly 200 of the electromechanical surgical system 10; to selectively rotate the end effector 300 about the longitudinal axis "X" and relative to the handle housing 102 of the surgical device 100; to selectively move, approximate, or separate an anvil assembly 310 and a cartridge assembly 320 of the end effector 300 relative to one another; and/or to fire a stapling and cutting cartridge (not shown) disposed within the cartridge assembly 320 of the end effector 300.

As best illustrated in FIG. 1A, the handle housing 102 of the surgical device 100 defines a connection portion 104 configured to accept a proximal portion of the adapter assembly 200 of the electromechanical surgical system 10. The connection portion 104 of the surgical device 100 houses a trigger contact surface 105 that is in electrical communication with the circuit board and a plurality of rotatable drive shafts or connectors 106 of the surgical device 100. Each rotatable drive shaft of the plurality of rotatable drive shafts 106 can be independently and/or dependently actuatable and rotatable by the one or more motors 112 housed within the housing handle 102 of the surgical device 100. In embodiments, the plurality of rotatable drive shafts 106 includes rotatable drive shafts 106a, 106b, 106c, 106d, and 106e. Although generally illustrated as arranged in a common plane or in line with one another, it is contemplated that the plurality of rotatable drive shafts 106 may be arranged in any suitable configuration such as a quadrant or matrix, for example. The one or more motors 112 of the surgical device 100 may be configured to selectively drive one drive shaft of the plurality of drive shafts 106 at any given time.

With continued reference to FIG. 1A, the handle housing 102 of the surgical device 100 supports a plurality of finger-actuated control buttons, rocker devices, and the like for activating various functions of the surgical device 100. For example, the handle housing 102 supports a plurality of actuators including, for example, an articulating pad such as articulating pad 108, to effectuate articulation of the end effector 300. The articulating pad 108 of the handle housing 102 is configured to contact a plurality of sensors 108a that cooperate with the articulating pad 108 to enable omnidirectional articulation of the end effector 300 relative to the adapter assembly 200 of the electromechanical surgical system 10. In embodiments, one or more of the plurality of sensors 108a of the surgical device 100 may correspond to different yaw and/or pitch angles relative to the longitudinal axis "X," to which the end effector 300 may be moved upon activation of one or more of the plurality of sensors 108a.

For a detailed description of various internal components of and operation of exemplary electromechanical surgical systems, the components of which are combinable and/or interchangeable with one or more components of the electromechanical surgical systems 10 described herein, reference may be made to World Intellectual Property Publication No. WO 2009/039506, filed Sep. 22, 2008, and U.S Patent Application Publication No. 2011/0121049, filed on Nov. 20, 2009, the entire disclosures of each of which are hereby incorporated by reference.

Figure 3:
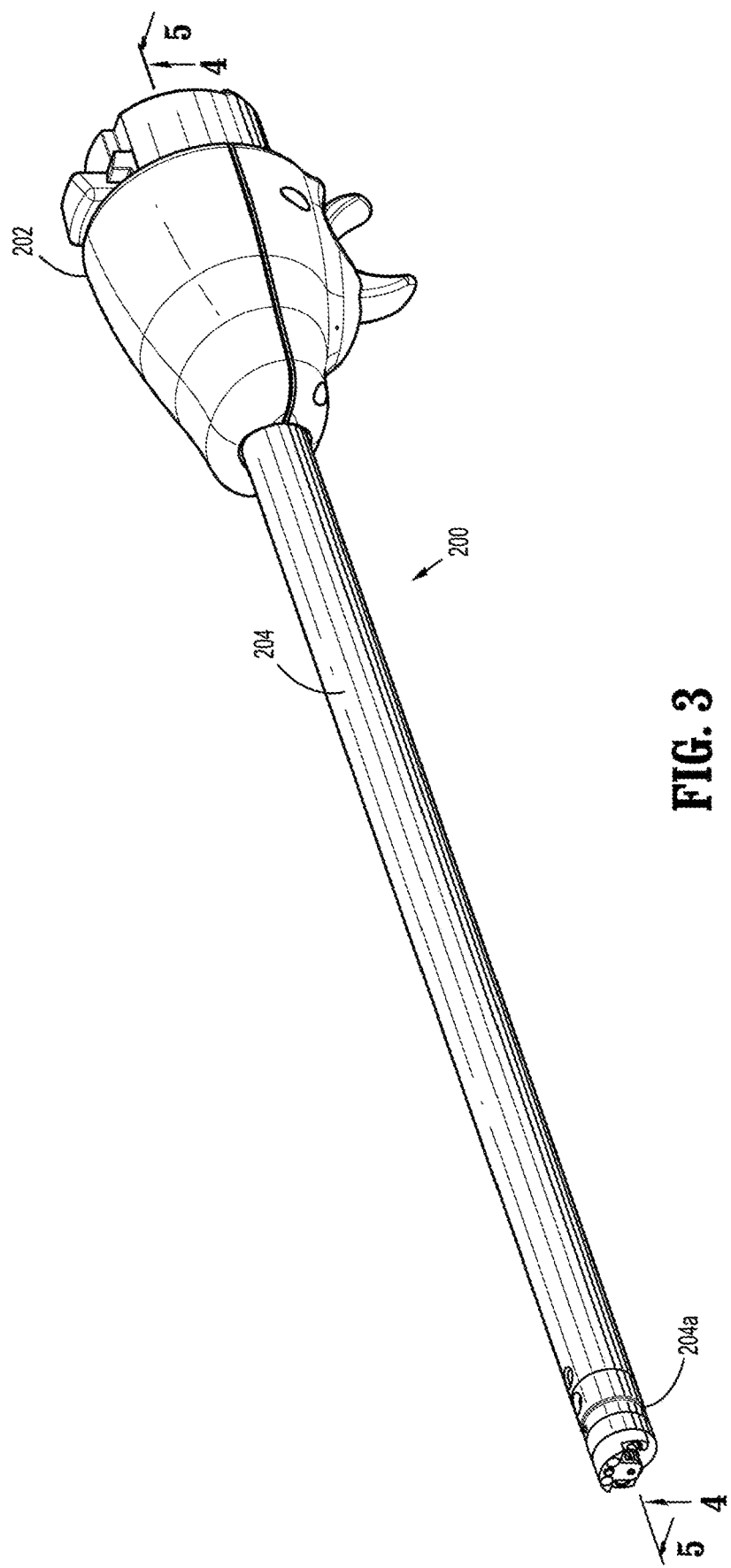
FIG. 3 is a perspective view of an adapter assembly of the electromechanical surgical system of FIG. 1A.
Figure 4:
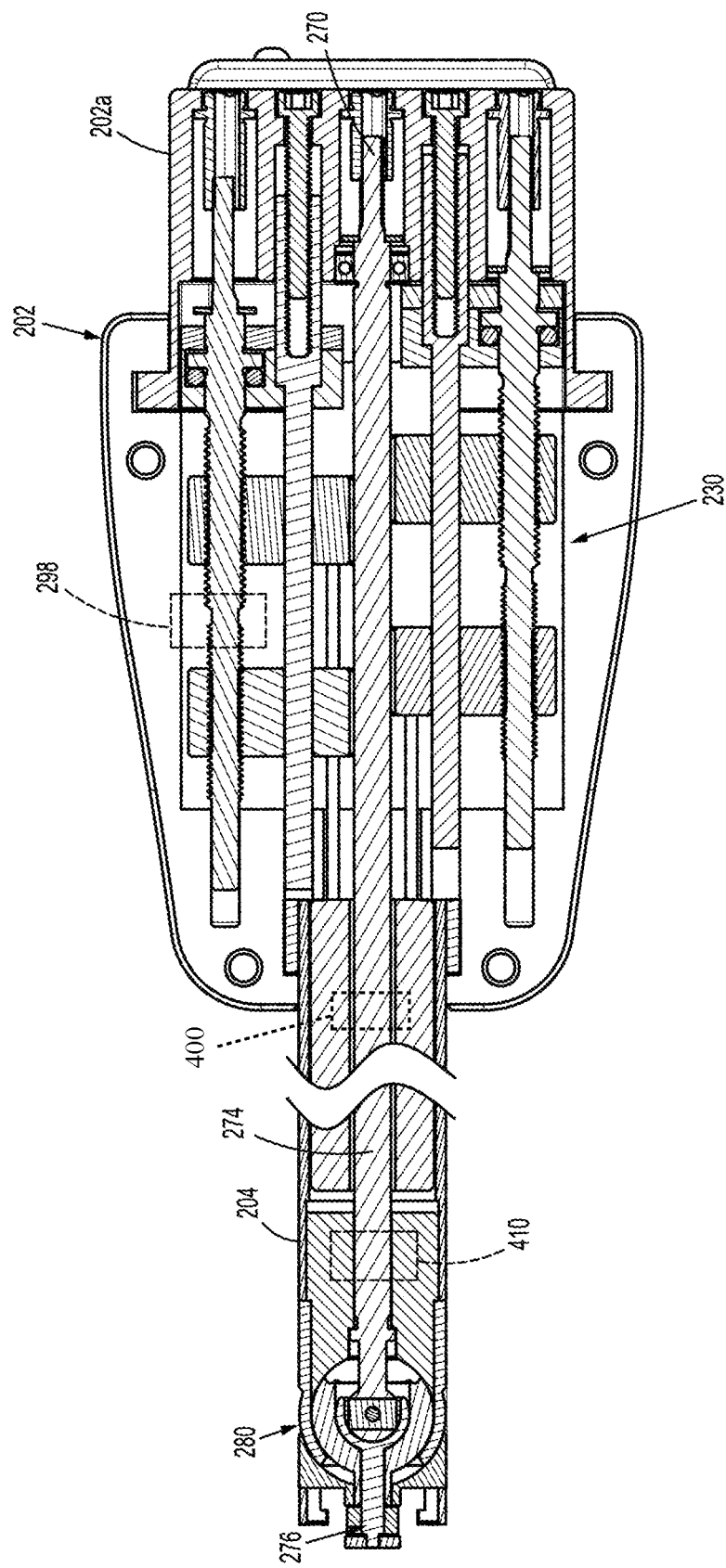
FIG. 4 is a bottom, cross-sectional view of the adapter assembly of FIG. 3, as taken along section line 4-4 of FIG. 3, illustrating an articulation assembly thereof in a first condition.
Figure 5:
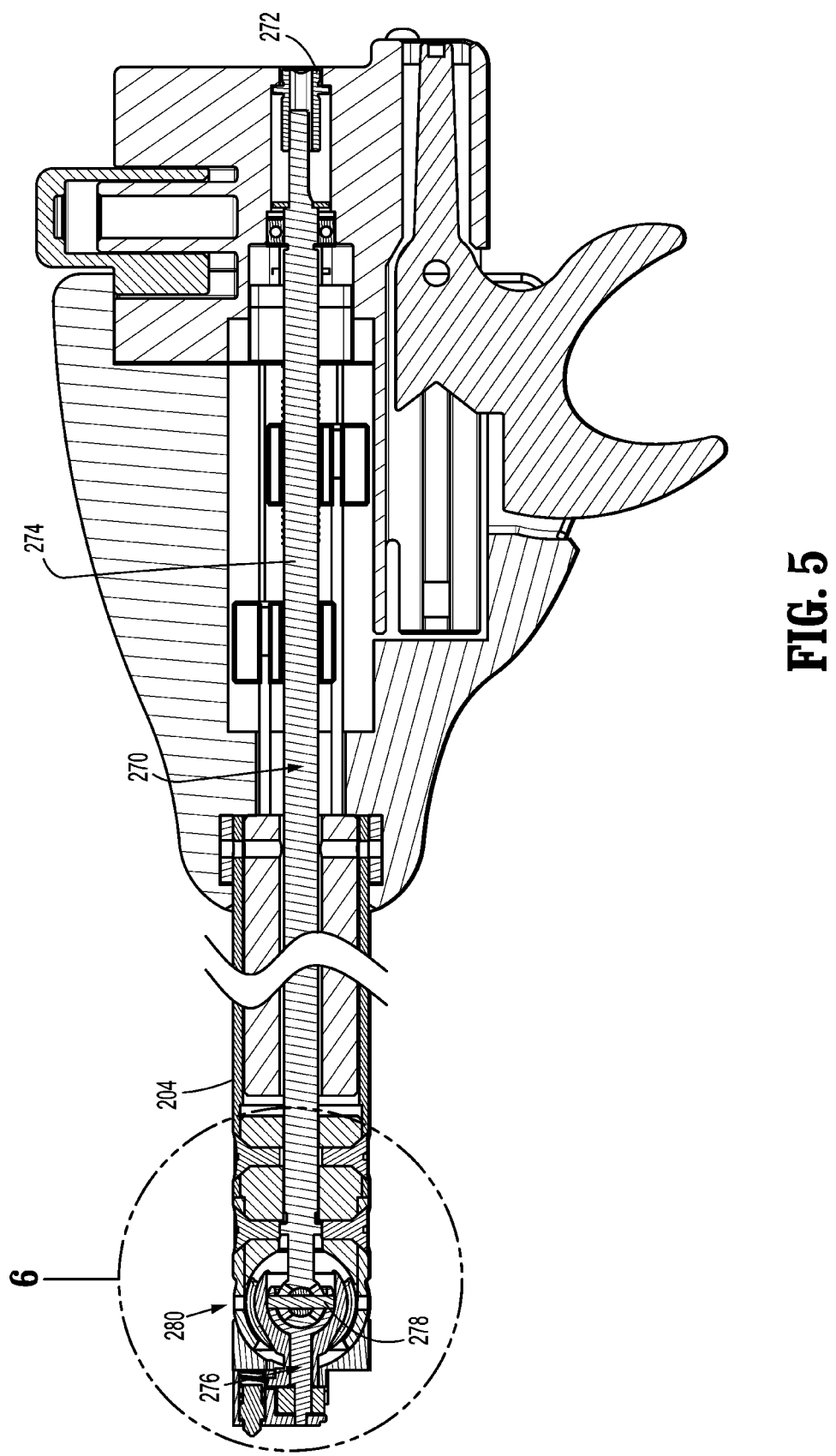
FIG. 5 is a side, cross-sectional view of the adapter assembly of FIG. 3, as taken along section line 5-5 of FIG. 3.
Figure 6:
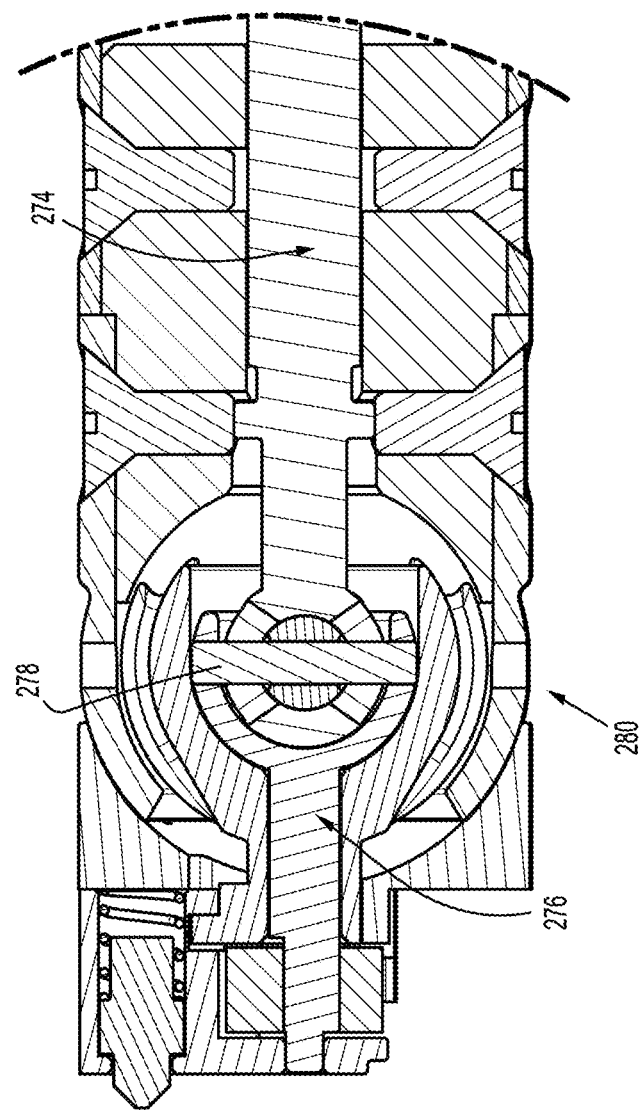
FIG. 6 is an enlarged, side, cross-sectional view of the indicated area of detail shown in FIG. 5.

Turning now to FIGS. 3 and 4, the adapter assembly 200 of the electromechanical surgical system 10 includes a housing 202 at a proximal end portion thereof and an outer tube 204 that extends distally from the housing 202 to a distal end portion 204a thereof. The housing 202 of the adapter assembly 200 includes a proximal housing 202a that is configured for selective engagement with a distal end portion of the handle housing 102. The housing 202 includes an articulation assembly 230 and a firing assembly 270 that are individually actuatable using the articulating pad 108 (FIG. 1A). A proximal portion of each of the articulation assembly 230 and the firing assembly 270 of the housing 202 are selectively engageable with a distal portion of a corresponding rotatable drive shaft 106 of the handle housing 102 when the adapter assembly 200 of the electromechanical surgical system 10 is coupled to the handle housing 102 of the surgical device 100 of the electromechanical surgical system 10. The articulation assembly 230 of the housing 202 is configured to effectuate articulation of the end effector 300 relative to the adapter assembly 200. The firing assembly 270 is configured to fire the stapling and cutting cartridge disposed within the cartridge assembly 320 of the end effector 300 (FIG. 1B). For a detailed description of an exemplary articulation assembly capable of use with the electromechanical surgical systems 10 described herein, reference may be made to U.S. Patent Application Publication No. 2015/0297199, filed on Apr. 21, 2014, the entire disclosure of which is incorporated by reference herein.

With reference to FIGS. 1A and 4-6, the firing assembly 270 of the electromechanical surgical system 10 is rotatably supported within the housing 202 and outer tube 204 of the adapter assembly 200. The firing assembly 270 includes an input socket 272 adapted to couple to a rotatable drive shaft 106 (FIG. 1A) of the housing handle 102, a proximal firing shaft 274 that extends distally from the input socket 272, a distal firing shaft 276 that extends distally from the proximal firing shaft 274, and a pin 278 that secures the proximal and distal firing shafts 274, 276 to one another. The proximal firing shaft 274, the distal firing shaft 276, and the pin 278 cooperate to define a universal joint 280 capable of transmitting rotational force from the corresponding rotatable drive shaft 106 of the surgical device 100 to the end effector 300 regardless of the articulation angle "a" of the end effector 300 with respect to the adapter assembly 200 (FIG. 2). For a detailed description of an exemplary firing assembly 270 capable of use with the electromechanical surgical system 10 described herein, reference may be made to U.S. Patent Application Publication No. 2015/0297199, previously incorporated by reference hereinabove.

In general, during normal operation of a standard universal joint, the rotational output speed of an output shaft of a universal joint is approximately equal to the rotational input speed of an input shaft of the universal joint when the universal joint is in an unarticulated orientation as the universal joint is rotated about a longitudinal axis thereof. As the output shaft of the universal joint is articulated relative to the input shaft of the universal joint, the output shaft speed of the universal joint becomes mismatched with the input shaft speed of the universal joint.

Figure 8:
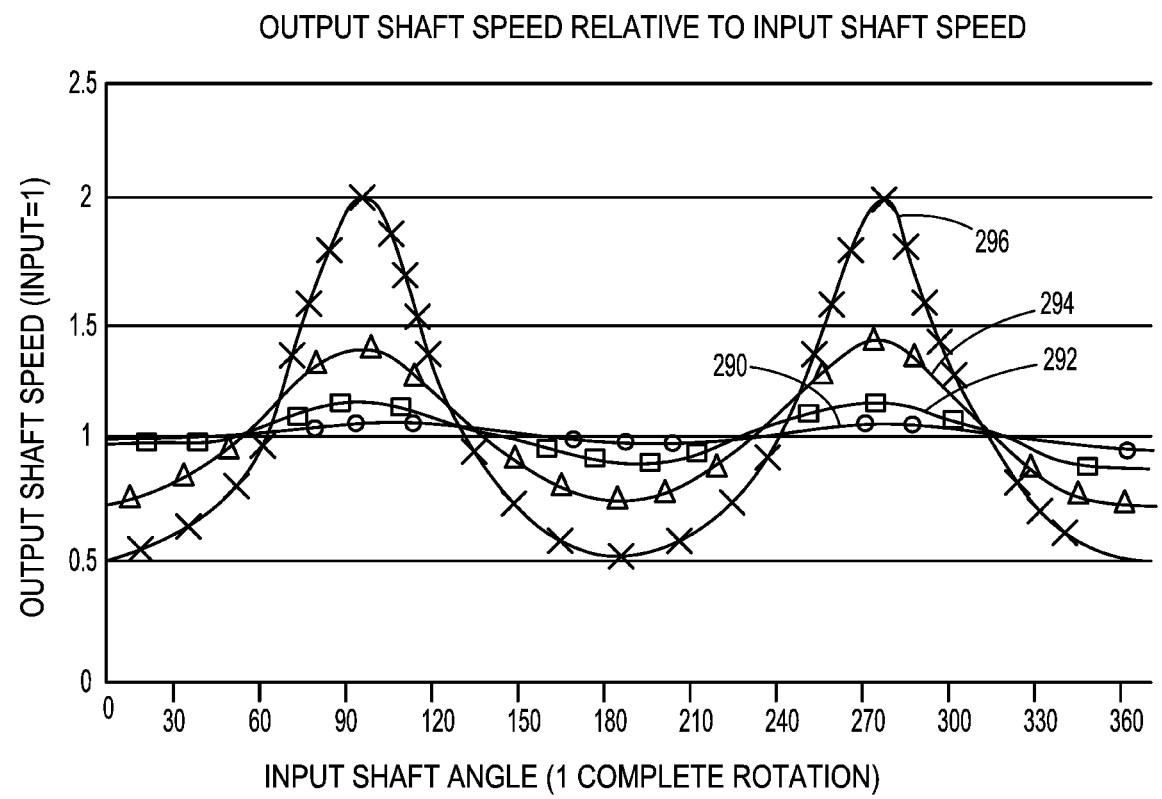
FIG. 8 is a graph of an output speed of a universal joint of the electromechanical surgical system of FIG. 1A relative to a rotational angle of the universal joint.

As best illustrated in FIG. 8, the output shaft speed of the universal joint while the universal joint is in an articulated position follows a sinusoidal profile (e.g., the output shaft speed increases and decreases relative to the input shaft speed over an angle of rotation of the universal joint) that increases in amplitude as the articulation angle of the output shaft of the universal joint is increased with respect to the input shaft of the universal joint. For example, when the output shaft of the universal joint is positioned at a first articulation angle "$\alpha_1$" of 15 degrees, a first curve 290 is defined through a single revolution (360 degrees) of the input shaft that minimally affects the output shaft speed of the universal joint. As the articulation angle "a" is increased, the amplitude of the sinusoidal profile correspondingly increases. Specifically, with reference to a second curve 292 corresponding to a second articulation angle "$\alpha_2$" of 30 degrees, a third curve 294 corresponding to a third articulation angle "$\alpha_3$" of 45 degrees, and a fourth curve 296 corresponding to a fourth articulation angle "$\alpha_4$" of 60 degrees, the output shaft speed of the universal joint increases or decreases at a corresponding increase in amplitude with respect to the input shaft speed of the universal joint (e.g., the output speed varies a greater amount as the articulation angle "$\alpha$" increases). As can be appreciated, the first through fourth curves 290, 292, 294, 294 are illustrative of the effect of articulation angle on the output shaft speed of the universal joint. In particular, a curve is developed for each possible articulation angle "$\alpha$" in which the universal joint is capable of being positioned. These curves may be generated by experimentation or may be generated using mathematical relationships such as interpolation, extrapolation or the like.

Figure 7:
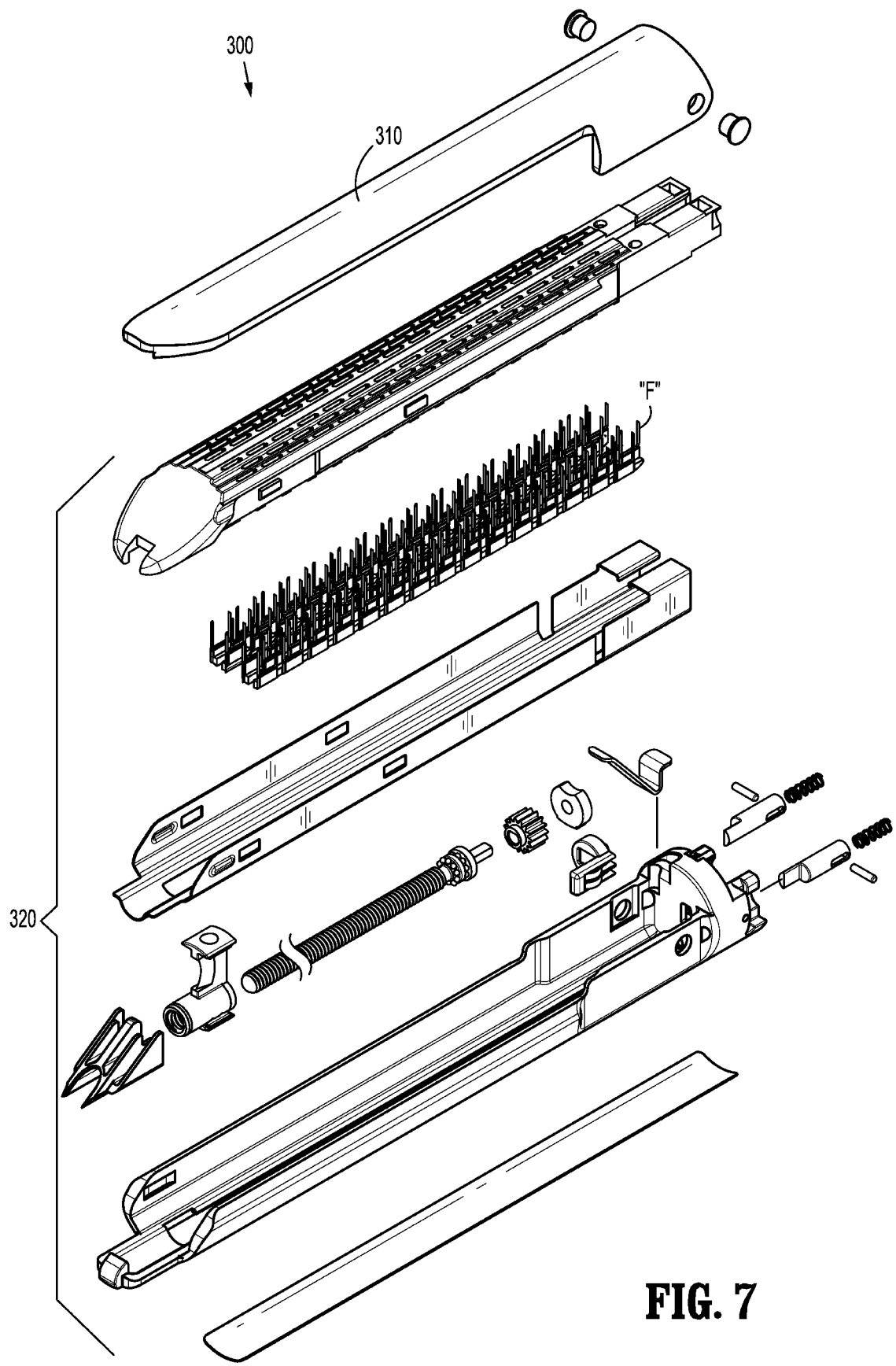
FIG. 7 is an enlarged, perspective view, with parts separated, of an end effector of the electromechanical surgical system of FIG. 1A.

Turning to FIGS. 1B and 7, the end effector 300 of the electromechanical surgical system 10 includes an anvil 310 and a cartridge assembly 320 that are movable between a first, open position, and a second, approximated or closed position. The anvil 310 and the cartridge assembly 320 of the end effector 300 cooperate to apply a plurality of linear rows of fasteners "F" (e.g., staples) to tissue. The cartridge assembly 320 is in mechanical communication with the distal firing shaft 276 (FIG. 6) of the firing assembly 270 such that actuation of the firing assembly 270 effectuates firing of the fasteners "F" from the cartridge assembly 320. For a detailed description of an exemplary end effector 300 capable of use with the electromechanical surgical systems 10 described herein, reference may be made to U.S. Patent Application Publication No. 2015/0297199, previously incorporated by reference hereinabove.

Figure 9:
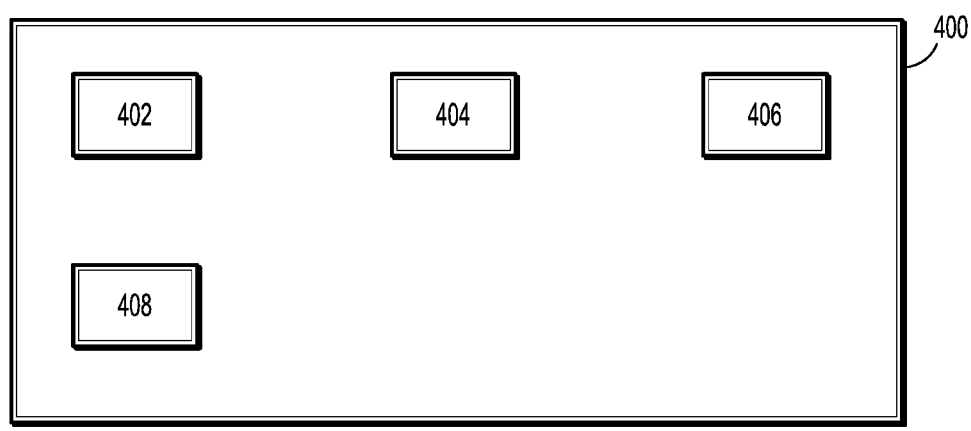
FIG. 9 is a block diagram of a correction unit of the electromechanical surgical system of FIG. 1A.

To prevent the non-uniform rotational output shaft speed of the universal joint 280, the electromechanical surgical system 10 includes a correction unit 400 (FIG. 9). Although generally illustrated as being disposed within a portion of the handle assembly 102 (FIG. 1A) of the surgical device 100, the correction unit 400 may be partially or wholly disposed in the adapter assembly 200. The correction unit 400 may be in electrical communication with the circuit board (not shown) via the trigger contact surface 105 (FIG. 1A) or any other suitable mechanical or electrical structure for transmitting electrical signals. The correction unit 400 may be integrated within the circuit board or in embodiments, may be an integrated circuit.

The correction unit 400 of the electromechanical surgical system 10 includes a memory 402, a processor 404 associated with the memory 402, a counter 406 in electrical communication with the processor 404, and a measuring unit 408 for measuring articulation angle "$\alpha$" of the end effector 300 relative to the adapter assembly 200. The memory 402 of the correction unit 400 may include any non-transitory computer-readable storage media for storing data and/or software that is executable by the processor 404 of the correction unit 400 (e.g., solid-state, volatile, non-volatile, removable, and/or non-removable). The memory 402 includes information stored therein that, when executed by the processor 404, causes the one or more motors 112 of the surgical device 100 to adjust its output speed.

An articulation angle "$\alpha$" of the end effector 300 of the electromechanical surgical system 10 relative to the adapter 200 of the electromechanical surgical system 10 may be measured using an articulation sensor 298 (FIG. 4), which may be any suitable device capable of measuring an angle of one component relative to another, such as an accelerometer, counter mechanism coupled to the articulation assembly 230 of the adapter 200 (e.g., rotary encoder, optical encoder, magnetic encoder, linear encoder, hall effect sensor, linear variable differential transformer (LVDT), inertial measurement unit (IMU), micromechanical system (MEMS), gyroscope, etc., or combinations thereof). The articulation sensor 298 may be supported, for example, within the housing 202 or outer tube 204 of the adapter assembly 200.

The correction unit 400 of the electromechanical surgical system 10 may be further configured to identify the rotational position of the universal joint 280 of the adapter assembly 200. The rotational position of the universal joint 280 dictates the difference between the output shaft speed and the input shaft speed of the universal joint 280 (see FIG. 8). For instance, if the articulation angle "$\alpha$" of the output shaft of the universal joint 280 is 60 degrees, e.g., the fourth curve 296 and articulation angle "$\alpha_4$," at a first position, the output shaft speed is 0.5 of the input shaft speed. As the universal joint 280 rotates, the difference in shaft speed increases until the output shaft speed difference reaches a peak of 2 times the input shaft speed at 90 degrees. The output shaft speed follows this sinusoidal profile throughout the 360 degree revolution of the universal joint 280. Accordingly, in order to compensate for the difference in output shaft speed of the universal joint 280, the rotational position of the universal joint 280 must be known. In this manner, the rotational position of the universal joint 280 may be measured using any suitable device capable of measuring rotational position, such as a counter, encoder, gyroscope, etc., or combinations thereof. In one non-limiting embodiment, the rotational position of the universal joint 280 may be measured using a rotary encoder 410 (FIG. 4) operably coupled to the firing shaft 274 of the firing assembly 270. In some embodiments, the rotary encoder 410 may be coupled to the motor 112 of the surgical device 100 or any other rotating component associated with the firing assembly 270 of the adapter assembly 200.

In order to ensure that the output shaft speed of the universal joint 280 of the adapter assembly 200 is maintained at a constant or substantially constant speed, data pertaining to the relationship between the output speed of the motor 112 of the surgical device 100 and the output shaft speed of the universal joint 280 is stored in the memory 402 of the correction unit 400. The output speed of the motor 112 is manipulated through each complete rotation thereof, the amount of which is dependent upon the articulation angle "α" of the output shaft of the universal joint 280. In embodiments, a constant output speed may have a tolerance of +/−2% as compared to the input speed and a substantially constant output speed may have a tolerance of +/−5% as compared to the input speed.

A unique motor speed profile 412 may be generated and stored in the memory 402 of the correction unit 400. The motor speed profile 412 can correspond to a known sinusoidal profile of the output shaft speed of the universal joint 280 at a specific articulation angle "α." The motor speed profile 412 can function to increase or decrease the output speed of the motor 112 in order to compensate for the natural increase or decrease in output shaft speed of the universal joint 280 as it completes each revolution. The motor speed profile 412 may vary the voltage applied to the motor 112 to increase or decrease the motor 112 speed using any suitable electrical structure, such as a potentiometer, pulse width modulation, etc., or combinations thereof. The processor 404 of the correction unit 400 is configured to receive a signal (e.g., electrical) or data indicative of the articulation angle "α" of the output shaft of the universal joint 280 and is configured to associate the articulation angle "α" data with a particular motor speed profile 412. In embodiments, the motor speed profile 412 may be stored in a look-up table or other reference source for quickly correlating the articulation angle "α" data with a corresponding motor speed profile 412 (and its data or information). In embodiments, the correction unit 400 may continuously and/or dynamically change the motor speed profile 412 in response to changes in the articulation angle "α" of the end effector 300 during firing of the fasteners "F" of the end effector 300.

Figure 10:
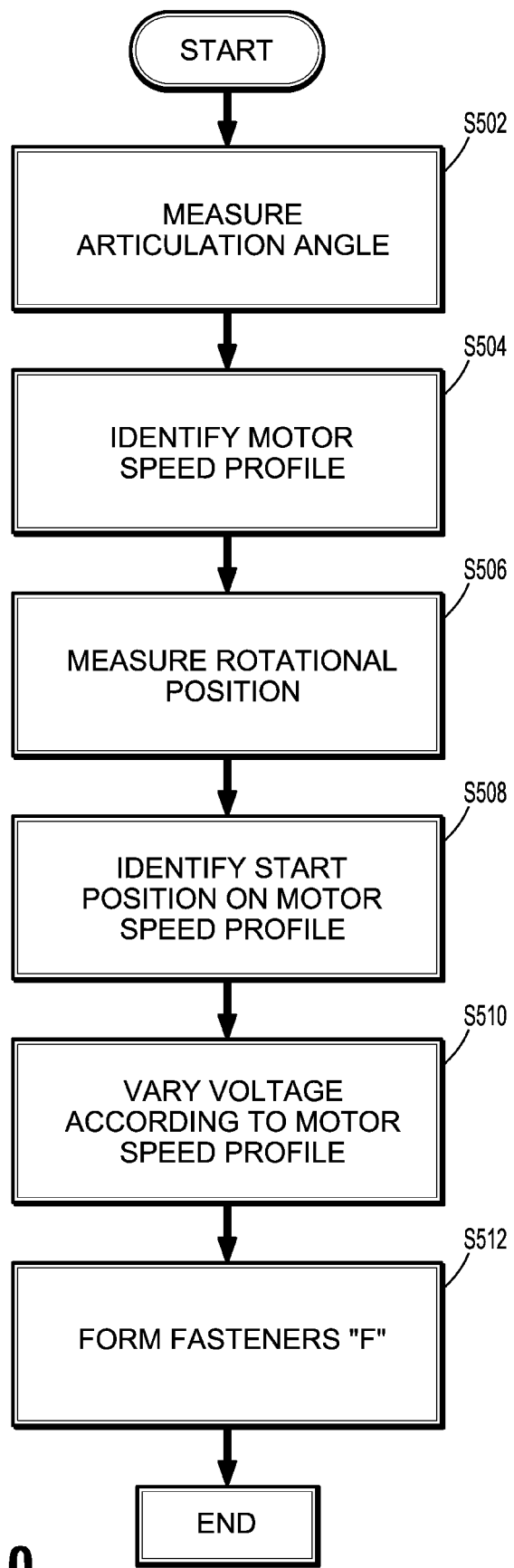
FIG. 10 is a flow chart of a method of using the electromechanical surgical system of FIG. 1A.

With reference to FIG. 10, in use, after the clinician has clamped target tissue, in step S502, the articulation angle "α" of the universal joint 280 is measured using the articulation sensor 298 of the adapter assembly 200. The articulation angle "α" of the universal joint 280 may be continuously monitored by the articulation sensor 298. In step S504, the correction unit 400 is configured to identify a motor speed profile 412 corresponding to the measured articulation angle "α." Once the motor speed profile 412 is identified, the rotational position of the universal joint 280 can be measured using the rotary encoder 410 or the like in step S506. In step S508, the rotational position of the universal joint 280 is configured to enable the correction unit 400 to identify a position on the motor speed profile 412 at which to start the motor 112. The output shaft speed of the universal joint 280 is configured to remain constant or substantially constant if the motor 112 is started at the correct location on the motor speed profile 412. In step S510, voltage may be applied to the motor 112 so that the speed of the motor 112 can be varied according to the selected motor speed profile 412. The voltage may be applied to the motor 112 until all of the fasteners "F" within the cartridge assembly 320 are formed, at which point, the motor 112 may be reversed and positioned in a home position in step S512. This method may be repeated as many times as the clinician desires or can depend upon the particular needs of the procedure being performed.

Although described in connection with a stapling device, the presently disclosed electromechanical surgical devices can be any suitable electromechanical instrument such as forceps, tack applier, clip applier, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the clinician to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s).

The master handles may include various sensors to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the clinician with enhanced tactile feedback simulating actual operating conditions. The master handles may also include a variety of different actuators for delicate tissue manipulation or treatment further enhancing the clinician's ability to mimic actual operating conditions.

Figure 11:
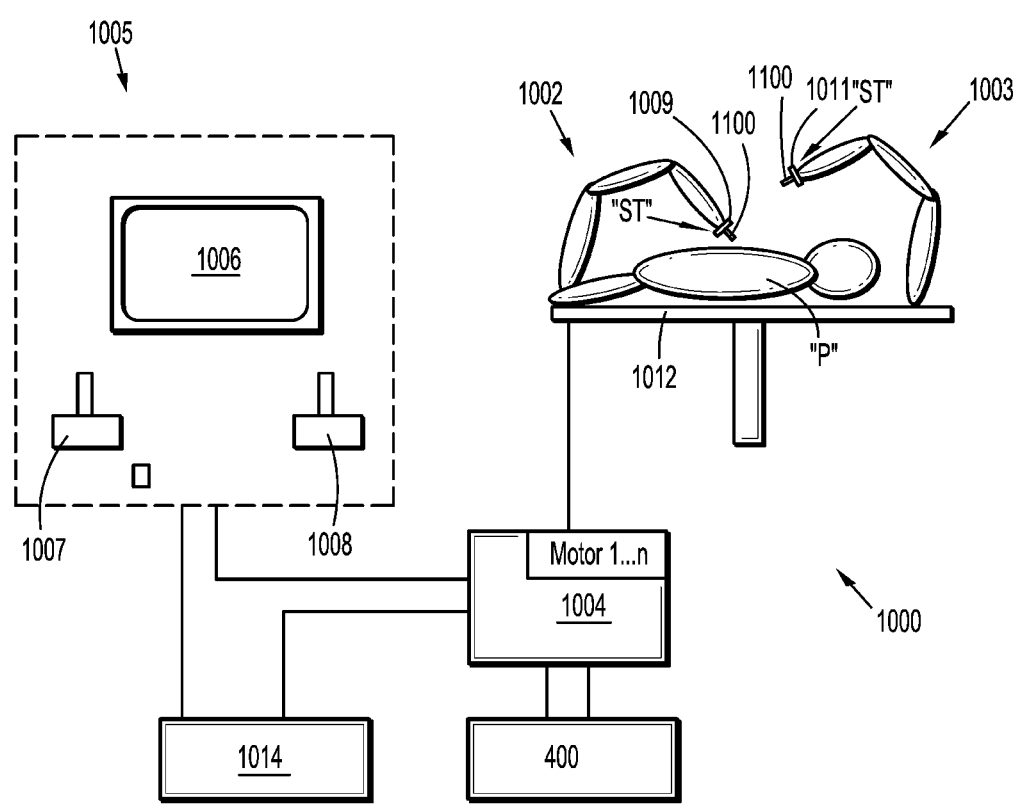
FIG. 11 is a schematic illustration of a medical work station and operating console in accordance with the present disclosure.

Referring also to FIG. 11, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members).

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) execute a desired movement according to a movement defined by means of the manual input devices 1007, 1008. The control device 1004 may also be set up in such a way that it regulates the movement of the robot arms 1002, 1003 and/or of the drives. The correction unit 400 may be in electrical communication with the control device 1004 and, in embodiments, may be integrated therein.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A surgical system, such as the presently disclosed surgical system, may also be attached to the additional robot arm. The medical work station 1000 may include a database 1014 coupled with the control device 1004. In some embodiments, pre-operative data from patient/living being "P" and/or anatomical atlases may be stored in the database 1014. For a more detailed description of exemplary medical work stations and/or components thereof, reference may be made to U.S. Patent Application Publication No. 2012/0116416, filed on Nov. 3, 2011, entitled "Medical Workstation" and PCT Application Publication No. WO2016/025132, filed on Jul. 21, 2015, entitled "Robotically Controlling Mechanical Advantage Gripping, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A method of operating a surgical system, the method comprising:
    articulating an end effector relative to an adapter assembly via a universal joint rotatably disposed between the end effector and the adapter assembly;
    measuring an articulation angle of the universal joint;
    identifying a motor speed profile having a mathematical curve based on a trigonometric function stored within a memory associated with a correction unit corresponding to the measured articulation angle of the universal joint; and
    manipulating an output speed of a motor operably coupled to the universal joint, according to the motor speed profile, to generate a substantially constant output speed from the universal joint.

2. The method according to claim 1, further including measuring a rotational position of the universal joint.

3. The method according to claim 2, wherein identifying the motor speed profile includes identifying the motor speed profile within the memory associated with the correction unit corresponding to the measured articulation angle and measured rotational position of the universal joint.

4. The method according to claim 2, wherein measuring the rotational position of the universal joint includes measuring the rotational position of the universal joint using a rotation sensor operably coupled to the universal joint.

5. The method according to claim 4, wherein measuring the rotational position of the universal joint includes measuring the rotational position of the universal joint using a rotary encoder operably coupled to the universal joint.

6. The method according to claim 2, wherein manipulating an output speed of the motor includes identifying a location within the identified motor speed profile based on the measured rotational position of the universal joint.

7. The method according to claim 6, wherein manipulating an output speed of the motor includes starting the motor at a speed associated with the identified location within the identified motor speed profile.

8. The method according to claim 1, further including firing a plurality of fasteners from the end effector.

9. The method according to claim 8, wherein firing a plurality of fasteners includes firing a plurality of surgical staples from a cartridge assembly disposed in the end effector.

10. The method according to claim 1, wherein measuring the articulation angle of the universal joint includes measuring the articulation angle of the universal joint using an articulation sensor operably coupled to the universal joint.

11. The method according to claim 10, wherein measuring the articulation angle of the universal joint includes measuring the articulation angle of the universal joint using an encoder.

12. The method according to claim 1, wherein identifying a motor speed profile includes identifying a motor speed profile from a plurality of motor speed profiles stored within the memory associated with the correction unit.

13. A method of operating a surgical system, the method comprising:
    articulating an end effector relative to an adapter assembly via a universal joint rotatably disposed between the end effector and the adapter assembly;
    measuring an articulation angle of the universal joint;
    identifying a sinusoidal motor speed profile stored within a memory associated with a correction unit corresponding to the measured articulation angle of the universal joint; and
    manipulating an output speed of a motor operably coupled to the universal joint, according to the sinusoidal motor speed profile, to generate a substantially constant output speed from the universal joint.

14. The method according to claim 13, further including selectively measuring a rotational position of the universal joint.

15. The method according to claim 14, wherein identifying the sinusoidal motor speed profile includes identifying the sinusoidal motor speed profile within a memory associated with the correction unit corresponding to the measured articulation angle and measured rotational position of the universal joint.

16. The method according to claim 14, wherein measuring the rotational position of the universal joint includes measuring the rotational position of the universal joint using a rotation sensor operably coupled to the universal joint.

17. The method according to claim 13, further including firing a plurality of fasteners from the end effector.

18. The method according to claim 17, wherein firing a plurality of fasteners includes firing a plurality of surgical staples from a cartridge assembly disposed in the end effector.

19. The method according to claim 13, wherein measuring the articulation angle of the universal joint includes measuring the articulation angle of the universal joint using an articulation sensor operably coupled to the universal joint.

20. The method according to claim 13, wherein identifying a motor speed profile includes identifying a motor speed profile from a plurality of motor speed profiles stored within the memory associated with the correction unit.

\* \* \* \* \*